United States Patent [19]

Komi

[11] Patent Number: 5,128,545
[45] Date of Patent: Jul. 7, 1992

[54] METHOD AND APPARATUS FOR BACKGROUND CORRECTION IN ANALYSIS OF A SPECIMEN SURFACE

[75] Inventor: Hideto Komi, Kyoto, Japan
[73] Assignee: Shimadzu Corporation, Kyoto, Japan
[21] Appl. No.: 680,427
[22] Filed: Apr. 4, 1991

[30] Foreign Application Priority Data

Apr. 19, 1990 [JP] Japan .................................. 2-103363

[51] Int. Cl.⁵ .............................................. G01N 23/20
[52] U.S. Cl. ..................... 250/310; 250/307; 250/397; 378/46
[58] Field of Search ............... 250/306, 307, 310, 311, 250/397; 378/45, 46; 364/498; 324/158 P

[56] References Cited

U.S. PATENT DOCUMENTS

| | | | |
|---|---|---|---|
| 4,219,731 | 8/1980 | Migitaka | 250/310 |
| 4,697,080 | 9/1987 | King | 250/307 |
| 4,980,639 | 12/1990 | Yoshizawa et al. | 250/310 |
| 5,055,679 | 10/1991 | Ninomiya et al. | 250/306 |

Primary Examiner—Jack I. Berman
Assistant Examiner—James Beyer
Attorney, Agent, or Firm—Wegner, Cantor, Mueller & Player

[57] ABSTRACT

A method and apparatus for background correction of the measured data in analysis of a specimen surface by scanning the surface with an electron beam, wherein a signal occurring from an element to be analyzed contained in the specimen is detected to obtain a two-dimensional distribution data of the level of the signal in a predetermined area of the specimen surface; a specimen current induced in the specimen by the scanning is detected to obtain a two-dimensional distribution data of the specimen current in the predetermined specimen surface area; a relation between the background intensity and specimen current of the specimen is calculated from the background intensity and specimen current measured on at least two points in the specimen surface area; a two-dimensional distribution data of the background intensity is calculated from the two-dimensional distribution data of the specimen current by using the calculated relation; and the calculated two-dimensional distribution data of the background intensity is subtracted from the two-dimensional distribution data of the signal level thereby to make a background correction of the distribution data of the signal level.

12 Claims, 2 Drawing Sheets (a) CHARACTERISTIC X-RAY PEAK DATA (b) SPECIMEN CURRENT DISTRIBUTION DATA (c) BACKGROUND INTENSITY DISTRIBUTION DATA (d) CHARACTERISTIC X-RAY PEAK DATA CORRECTED FOR BACKGROUND

METHOD AND APPARATUS FOR BACKGROUND CORRECTION IN ANALYSIS OF A SPECIMEN SURFACE

BACKGROUND OF THE INVENTION

This invention relates to a method and apparatus for analyzing the surface of a specimen with such as an electron probe microanalyzer (EPMA), a scanning electron microscope (SEM) and the like, and more particularly to background correction of the measured data in such surface microanalyzers.

In an electron microanalyzer or a scanning electron microscope, the surface of a specimen to be analyzed is scanned by an electron beam having a diameter of several tens of angstroms, so that the various kinds of information emerging from each and every minute point on the specimen surface scanned by the electron beam are electrically detected, and displayed in terms of composition of the specimen and/or concentration of the components thereof on a cathode-ray tube in synchronism with the scanning of the specimen surface thereby to display the distribution of the elements contained in the specimen.

Various signals emerge from a specimen surface irradiated by an electron beam. Depending upon which of the signals is used for formation of images, a secondary electron image, a reflected electron image, a luminescence image, a characteristic X-ray image, an Auger electron image, etc. can be observed.

In the above-mentioned surface analysis by means of, for example, characteristic X rays, the peaks of the characteristic X rays emitted by the component elements of the specimen under examination are superimposed on a background caused by the inherent characteristic of the instrument, the conditions of excitation of the specimen and the composition of the specimen. This means that the measured data of the distribution of the elements in the specimen contain errors caused by background. Therefore, it is customary to correct the measured data for the background.

There are known various methods of backgrounds correction. In one of them, a measurement of background is conducted all over the specimen surface before or after scanning the specimen surface, and the measured value is corrected for the background. In another of the known methods, background is measured on some separate points on a specimen surface, and from the measured data the background of the whole specimen surface is surmised thereby to make a background correction of the measured value.

Japanese Unexamined Patent Publication No. 2-10639 discloses a third method of background correction which uses two X-ray spectrometers for each element to be analyzed. The focal points of the two X-ray spectrometers are so set as to coincide on the surface of a specimen to be analyzed, and one of the spectrometers is set to an X-ray wavelength characteristic of an element to be measured contained in the specimen while the other spectrometer is set to a wavelength adjacent to the base of the above-mentioned characteristic X-ray peak wavelength of the element to be measured, and the specimen surface is scanned by both spectrometers simultaneously thereby to obtain both the characteristic X-ray data of the element being measured containing background and the background data at the same time for background correction of the measured data of the specimen.

In the first method, since a measurement of background is conducted all over the surface of a specimen to be analyzed before or after scanning the specimen surface for measurement, the specimen surface is scanned twice, so that a long time is required for analysis of the specimen surface.

In the second method, since background is measured skippingly at several points on the surface of a specimen, the time required for measurement is advantageously shorter than in the first method. Background, however, is caused by not only the characteristic of the instrument and the exciting conditions of the specimen but also the composition of the elements present at the measured spots on the specimen surface, so that accurate background correction cannot be effected.

The third method which uses two X-ray spectrometers for each element to be analyzed has solved the problems involved in the time required for analysis and adverse influences by the elemental composition at the measured spots of the specimen surface. However, two X-ray spectrometers are required for each element to be measured, so that the whole apparatus becomes bulky with an increased manufacturing cost.

SUMMARY OF THE INVENTION

To overcome the above-mentioned and other defects and disadvantages in the prior art, this invention provides a method and apparatus for analyzing the surface of a specimen which is capable of making an accurate background correction without increasing the equipment and the time required for analysis.

Generally, the electron probe microanalyzer or the scanning electron microscope is provided with a detector for detecting specimen current the value of which is correlated with the average atomic number of the elements contained in the specimen. Also, the value of background in the measured data of characteristic X rays, Auger electrons, etc. is correlated with the average atomic number. Therefore, if the specimen current and the background intensity of a specimen to be analyzed are measured under the same condition as that under which the distribution data of an element in the specimen is measured and an expression of the relation between the specimen current and the background intensity is formulated, it is possible to correct the measured distribution data of the element for background by the specimen current value by using the expression of the above relation.

Accordingly, the invention provides a method of background correction of the measured data in microanalysis of the surface of a specimen by irradiating a predetermined area of the specimen surface with an electron beam and detecting a signal caused by the irradiation to occur from an element to be analyzed in the specimen so as to obtain a two-dimensional distribution data of the level of the signal in the irradiated specimen surface area, comprising:

detecting a specimen current induced in the specimen by the irradiation of the specimen with the electron beam to obtain a two-dimensional distribution data of the value of the specimen current in the irradiated specimen surface area;

measuring the intensity of background and the value of the specimen current on at least one point in the predetermined specimen surface area;

formulating a relation between the background intensity and specimen current of the specimen from the measured background intensity and specimen current value on the one point in the specimen surface area;

calculating a two-dimensional distribution data of the background intensity from the two-dimensional distribution data of the specimen current value by using the formulated relation; and subtracting the calculated two-dimensional distribution data of the background intensity from the two-dimensional distribution data of the signal level thereby to make the two-dimensional distribution data of the signal level corrected for background.

The invention also provides an apparatus for analyzing the surface of a specimen, comprising:

means for producing an electron beam;

means for irradiating a predetermined area of the specimen surface with the electron beam;

first detecting means for detecting a signal caused by the irradiation to occur from the specimen so as to produce a first corresponding output signal;

second detecting means for detecting a specimen current induced in the specimen by the irradiation so as to produce a second corresponding output signal;

means for storing the first and second output signals;

means for correcting the first output signal for background; and means for controlling the irradiating means, storing means and background correcting means so as to formulate a relation between the background intensity and specimen current of the specimen from the first and second output signals detected on at least one point in the predetermined specimen surface area, calculate a distribution data of the background intensity in the predetermined specimen surface area from the distribution data of the specimen current contained in the second output signal detected in the predetermined specimen surface area by using the formulated relation, and subtract the calculated distribution data of the background intensity from the distribution data of the level of the first output signal detected in the predetermined specimen surface area thereby to provide a background-corrected distribution data of the level of the first output signal.

DESCRIPTION OF THE PREFERRED EMBODIMENT

Figure 1:
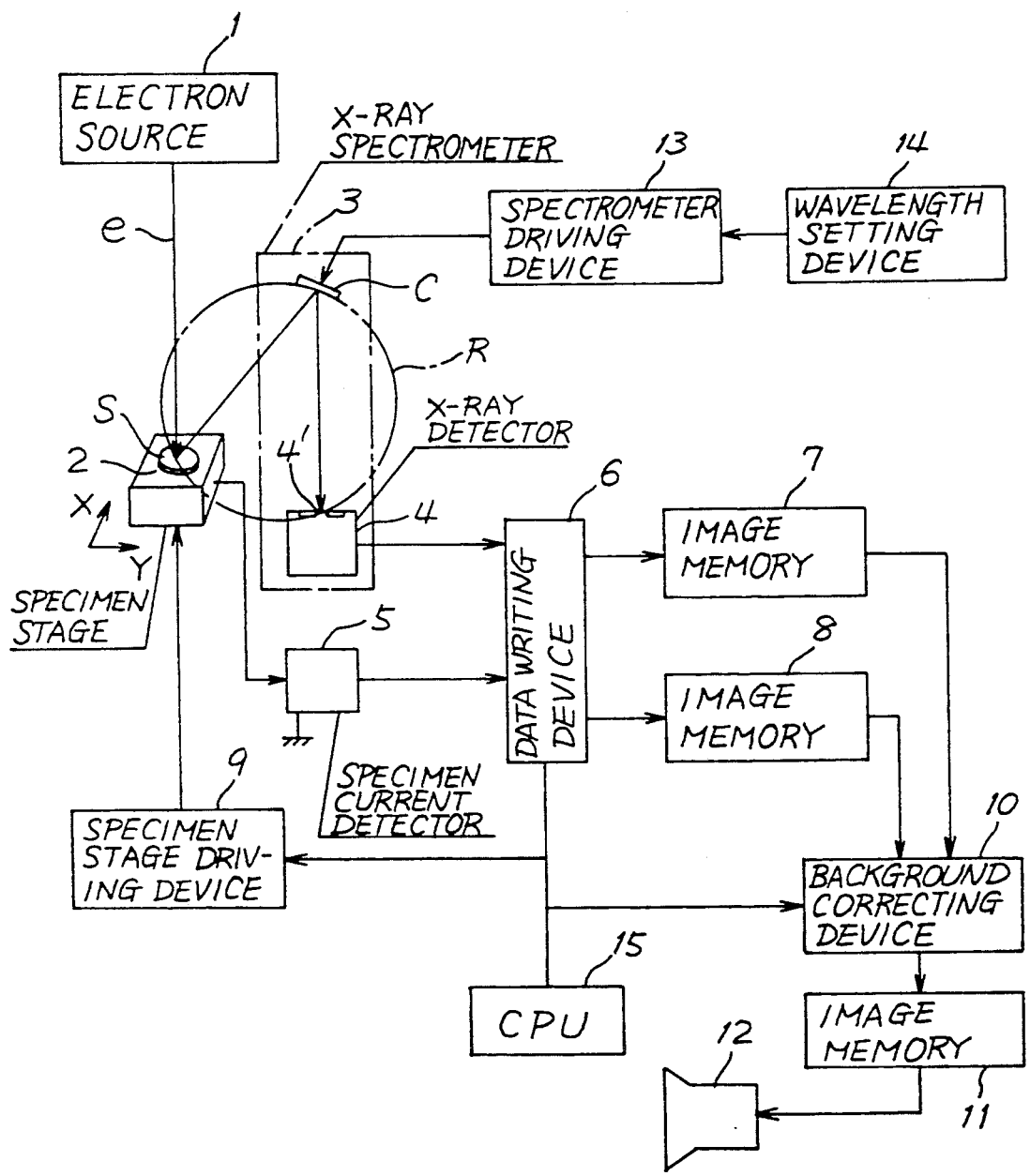
FIG. 1 is a block diagram of one embodiment of the invention.

Referring to FIG. 1 which schematically shows one embodiment of the invention in the form of an X-ray spectrometric analyzer which uses an electron probe microanalyzer.

Generally, this type of apparatus is provided with two to six spectrometers arranged about an electron optics for providing an electron beam to irradiate a specimen to be analyzed.

In FIG. 1, an electron source 1 produces an electron beam e to irradiate a specimen S to be analyzed. The specimen S is supported on a stage 2 which is movable in X- and Y-directions. The electron beam e irradiating the specimen S excites emission of X rays, which are directed to an X-ray spectrometer 3 comprising a crystal C having a curved surface, an X-ray detector 4 having a front slit 4', and means for connecting the crystal C and the X-ray detector 4 so that the crystal C and the front slit 4' of the X-ray detector 4 and the point on the specimen surface on which the electron beam e impinges are positioned on the circumference of a Rowland circle R, with the focal point of the X-ray spectrometer 3 coinciding with the point on the specimen surface on which the electron beam e impinges.

A specimen current detector 5 is provided to detect a specimen current induced in the specimen S by the electrons impinging thereon. A data writing device 6 is connected to the X-ray detector 4 and the specimen current detector 5. The device 6 performs an analog-to-digital conversion of the outputs from the detectors 4 and 5 and sends the data obtained by the conversion together with the information about the position of the specimen under examination to image memories 7 and 8, respectively, to be stores therein. A specimen stage driving device 9 drives the specimen stage 2 in X- and Y-directions by means of a pulse motor not shown. A background correcting device 10 conducts necessary operations on the data taken out of the memories 7 and 8 to provide background-corrected data for mapping the distribution of the element in the specimen surface being analyzed. The data is stored in an image memory 11 and displayed on a color cathode-ray tube 12.

A spectrometer driving device 13 sets the crystal C and the X-ray detector 4 to a position corresponding to a wavelength set by a wavelength setting device 14. A central processing unit 15 controls the above-mentioned and other necessary operations of the above-mentioned devices.

Figure 3:
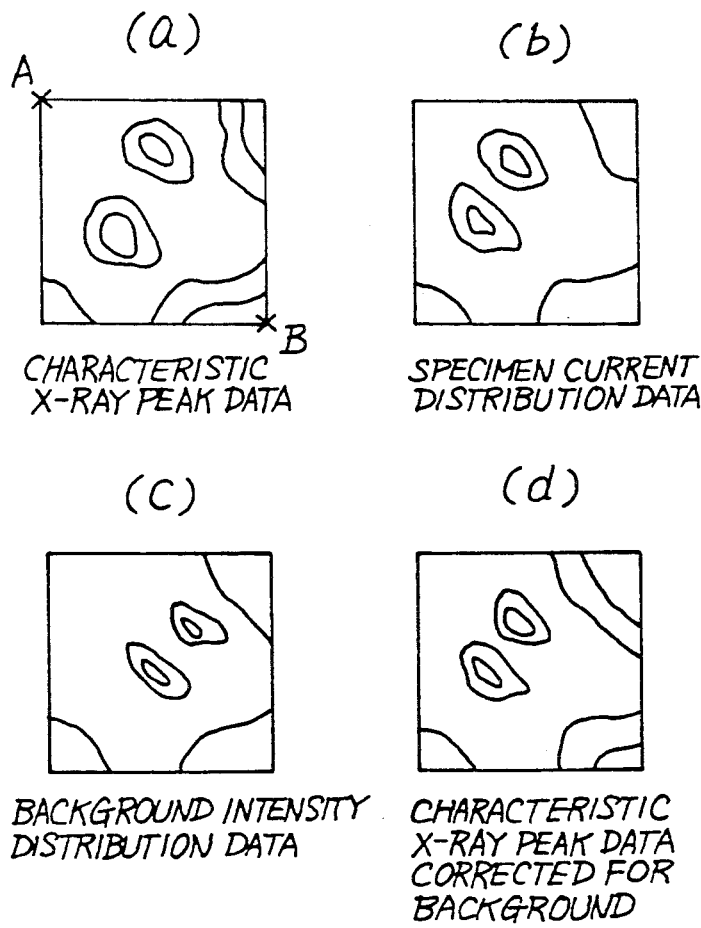
FIGS. 3(a), 3(b), 3(c) and 3(d) schematically show two-dimensional distribution data obtained in an analysis conducted in accordance with the invention.

In operation, when an analysis is started, the specimen stage driving device 9 is operated to move the specimen stage 2 so that the electron beam e is incident on a point A (FIG. 3(a)) on the specimen surface where scanning is to be started. On the other hand, the spectrometer driving device 13 is operated by the wavelength setting device 14 to set the crystal C to a wavelength at the base of an appropriate one of the characteristic X-ray peaks of an element to be analyzed. Under the condition, the specimen S is irradiated with the electron beam e, and the outputs from the X-ray detector 4 and the specimen current detector 5 are written by the data writing device 6 into the image memories 7 and 8, respectively. The outputs from the detectors 4 and 5 represent the background intensity and the specimen current, respectively, detected at the point A on the specimen surface.

Then, the spectrometer driving device 13 is operated by the wavelength setting device 14 to set the crystal C to the appropriate characteristic X-ray peak wavelength of the element to be analyzed. After that, while the specimen stage 2 is driven by the specimen stage driving device 9 to move the specimen S thereon in X- and or Y-direction thereby to scan the specimen surface by the electron beam e, the outputs from the X-ray detector 4 and the specimen current detector 5 are applied through the data writing device 6 to the image memories 7 and 8 to be stored therein, respectively. The output from the X-ray detector 4 stored in the image memory 7 contains a two-dimensional distribution data of the characteristic X-ray peak of the element to be analyzed as shown in FIG. 3(a), and the output from the specimen current detector 5 stored in the image memory 8 contains a two dimensional distributional data of the specimen current as shown in FIG. 3(b).

Figure 2:
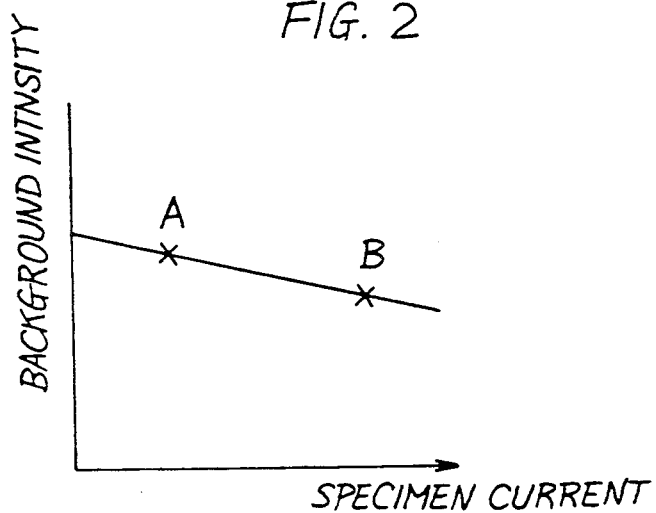
FIG. 2 is a graph showing a relation between the background intensity and the specimen current.

When the scanning of the specimen surface has been completed, at the point B (FIG. 3(a)) where the analysis has been finished the spectrometer driving device 13 is again operated by the wavelength setting device 14 to set the spectrometer 3 to the wavelength at the base of the appropriate characteristic X-ray peak of the element being analyzed, and the intensity of the background and the value of the specimen current at the point B are measured. The result of the measurements are stored in the memories 7 and 8, respectively. The background correcting device 10 forms from the background intensity and the specimen current value measured at the two points A and B on the specimen surface a graph of a relation between the background intensity and the specimen current as shown in FIG. 2. Using the relation of the graph shown in FIG. 2, the device 10 calculates a two-dimensional distribution data of the background intensity as shown in FIG. 3(c) from the two-dimensional distribution data of the specimen current shown in FIG. 3(b). Then, the background intensity distribution data (FIG. 3(c)) is subtracted from the characteristic X-ray peak data (FIG. 3(a)) of the element being analyzed which is stored in the image memory 7 thereby to obtain a background-corrected, true distribution data of the characteristic X-ray peak of the element as shown in FIG. 3(d). The data is stored in an image memory 11 and displayed on the cathode-ray tube 12. The CPU 15 controls the above operations.

In the illustrated embodiment, the background intensity and the specimen current are measured at both the starting and finishing points of analysis on the specimen. The measurement may also be made on any other points on the specimen. Background correction may also be made by detecting the background intensity and the specimen current at any single point of the specimen provided that the relation between the background intensity and the specimen current is known.

In the illustrated embodiment, the characteristic X rays are detected to provide a detection signal. It is also possible to detect secondary electrons, reflected electrons, luminescence, Auger electrons, etc. for the same purpose.

In the illustrated embodiment, the specimen stage is moved to scan the specimen with the electron beam. It is possible to scan the electron beam over the specimen surface.

In accordance with the invention, since background correction is conducted by utilizing the specimen current detector with which conventional electron probe microanalyzers and scanning electron microscopes are usually provided, it is not necessary to add to the existing equipment any particular device for background correction. Since the measured data of the whole specimen surface to be analyzed can be accurately corrected for background by measuring background at only one or two points on the specimen surface, the time required for analysis can be greatly shortened.

What I claim is:

1. A method of background correction of measured data obtained in analysis of a specimen surface by irradiating a predetermined area of said specimen surface with an electron beam and detecting a signal caused by said irradiation so as to obtain two-dimensional distribution data of a level of said signal, said signal containing a background component as well as a component caused by an element being analyzed in said specimen, and comprising the steps of:

detecting a specimen current induced in said specimen by said irradiation to obtain two-dimensional distribution data of a value of said specimen current in said predetermined specimen surface area;

measuring an intensity of said background component and a value of said specimen current at each of at least two points in said predetermined surface area;

formulating a relation between said background intensity and said specimen current from said background intensity and specimen current value obtained by said measuring at each of said at least two points in said specimen surface area;

calculating two-dimensional distribution data of said background intensity from said two-dimensional distribution data of said specimen current value by using said formulated relation; and subtracting said calculated two-dimensional distribution data of said background intensity from said two-dimensional distribution data of said signal level thereby to make said two-dimensional distribution data of said signal level corrected for background.

2. The method of claim 1, wherein said signal occurring from said specimen caused by said irradiation with said electron beam is in the form of at least one of the set of secondary electrons, reflected electrons, luminescence, Auger electrons, and X-rays.

3. The method of claim 1, wherein said irradiation of said predetermined specimen surface area is conducted by moving said electron beam so as to scan said predetermined specimen surface area.

4. the method of claim 1, wherein said irradiation of said predetermined specimen surface area is conducted by moving said specimen so as to make said electron beam scan said predetermined specimen surface area.

5. The method of claim 3, wherein said background intensity and said specimen current value are measured at a first point on said specimen surface area where said scanning is started and a second point thereon where said scanning is completed.

6. The method of claim 4, wherein said background intensity and said specimen current value are measured at a first point on said specimen surface area where said scanning is started and a second point thereon where said scanning is completed.

7. An apparatus for analyzing a surface of a specimen, comprising:

means for producing an electron beam;

means for irradiating a predetermined area of said specimen surface with said electron beam;

first detecting means for detecting a signal caused by said irradiating and for producing a first corresponding output signal containing a background component as well as a component caused by an element to be analyzed in said specimen;

second detecting means for detecting a specimen current induced in said specimen by said irradiating and for producing a second corresponding output signal;

means for storing said first and second output signals;

means for correcting said first output signal for said background; and means for controlling said irradiating means, storing means and background component correcting means so as to formulate a relation between an intensity of said background and said specimen current from said first and second output signals detected on each of at least two points in said predetermined specimen surface area;

means for calculating two-dimensional distribution data of said background intensity in said predetermined specimen surface area from two-dimensional distribution data of said specimen current contained in said second output signal by using said formulated relation; and means for subtracting said calculated two-dimensional distribution data of said background intensity from the two-dimensional distribution data of the level of said first output signal detected in said predetermined specimen surface area thereby to provide a background-corrected two-dimensional distribution data of the level of said first output signal.

8. The apparatus of claim 7, wherein said signal occurring from said specimen is in the form of at least one of the set of secondary electrons, reflected electrons, luminescence, Auger electrons, and X-rays.

9. The apparatus of claim 7, wherein said irradiating means comprises means for moving said specimen so that said electron beam scans said predetermined specimen surface area.

10. The apparatus of claim 7, wherein said irradiating means comprises means for moving said electron beam to scan said predetermined specimen surface area.

11. The apparatus of claim 9, wherein said control means controls said specimen moving means, storing means and background correcting means so as to formulate a relation between said background intensity and specimen current of said specimen from said first and second output signals detected at a first point on said predetermined specimen surface area where said specimen moving means causes said electron beam to start scanning of said predetermined specimen surface area and a second point on said predetermined specimen surface area where said specimen moving means causes said scanning to be completed.

12. The apparatus of claim 10, wherein said control means controls said electron beam moving means, storing means and background correcting means so as to formulate a relation between said background intensity and specimen current of said specimen from said first and second output signals detected at a first point on said predetermined specimen surface area where said electron beam moving means causes said electron beam to start scanning of said predetermined specimen surface area and a second point on said predetermined specimen surface area where said electron beam moving means causes said scanning to be completed.

* * * * *